United States Patent
Buelow et al.

(10) Patent No.: US 7,267,822 B2
(45) Date of Patent: *Sep. 11, 2007

(54) CYTOMODULATING LIPOPHILIC PEPTIDES FOR MODULATING IMMUNE SYSTEM ACTIVITY AND INHIBITING INFLAMMATION

(75) Inventors: Roland Buelow, Palo Alto, CA (US); Gèrard Grassy, Perols (FR); Bernard Calas, Montpellier (FR)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/780,321

(22) Filed: Feb. 17, 2004

(65) Prior Publication Data

US 2004/0248810 A1    Dec. 9, 2004

Related U.S. Application Data

(63) Continuation of application No. 09/028,083, filed on Feb. 23, 1998, now Pat. No. 6,696,545, which is a continuation-in-part of application No. 08/838,916, filed on Apr. 11, 1997, now abandoned.

(51) Int. Cl.
| | |
|---|---|
| A61K 38/00 | (2006.01) |
| A61K 38/03 | (2006.01) |
| A61K 47/00 | (2006.01) |
| A61K 47/10 | (2006.01) |
| A61K 47/18 | (2006.01) |
| A61K 31/045 | (2006.01) |
| C07K 7/06 | (2006.01) |

(52) U.S. Cl. .............. 424/185.1; 424/278.1; 514/2; 514/5; 514/724; 530/328; 530/345; 530/402

(58) Field of Classification Search ............. 530/328; 424/185.1; 514/2, 15
See application file for complete search history.

(56) References Cited

U.S. PATENT DOCUMENTS

| | | | |
|---|---|---|---|
| 5,385,888 A | 1/1995 | Goodenow et al. | |
| 5,702,946 A * | 12/1997 | Doerschuk et al. | ...... 435/320.1 |
| 5,723,128 A | 3/1998 | Clayberger et al. | |
| 5,753,625 A | 5/1998 | Buelow | |
| 6,162,434 A | 12/2000 | Buelow et al. | |
| 6,696,545 B1 * | 2/2004 | Buelow et al. | .............. 530/328 |
| 6,828,415 B2 * | 12/2004 | Engel et al. | ............... 530/300 |

FOREIGN PATENT DOCUMENTS

| | | |
|---|---|---|
| WO | WO88/05784 | 8/1988 |
| WO | WO90/10016 | 9/1990 |
| WO | WO93/03764 A1 * | 3/1993 |
| WO | WO93/08817 | 5/1993 |
| WO | WO93/17699 | 9/1993 |
| WO | WO94/02162 | 2/1994 |
| WO | WO95/13288 | 5/1995 |
| WO | WO96/22306 | 7/1996 |
| WO | WO96/35443 | 11/1996 |
| WO | WO97/24140 A1 | 7/1997 |
| WO | WO97/44052 A1 | 11/1997 |
| WO | WO97/44351 A1 | 11/1997 |

OTHER PUBLICATIONS

Abraham, R.J., et al., "Charge Calculations in Molecular Mechanics 7: Application to Polar Pi Systems Incorporating Nitro, Cyano, Amino, C=S and Thio Substituents," *J. Comput. Aided Molec. Des.* 3(2):175-187 (1989).

Ashton, M.J., et al., "New perspectives in lead generation II: Evaluating molecular diversity," *Disease Drug Ther.* 1(2):71-78 (Feb. 1996).

Bjorkman, P.J., et al., "Structure of the Human Class I Histocompatibility Antigen, HLA-A2," *Nature* 329(6139):506-512 (Oct. 1987).

Blaese, R.M., et al., "Gene therapy for primary immunodeficiency disease," *Immunodef. Rev.* 3(4):329-349 (Jan. 1992).

Buelow, R., et al., "Immunomodulation by soluble HLA class I," *Transplantation* 59:649-654 (Mar. 1995).

Buelow, R., et al., "Prolongation of Skin Allograft Survival in Mice Following Administration of ALLOTRAP," *Transplantation* 59(4):455-460 (Feb. 1995).

Cantoni, L., et al., "Interleukin-1 and tumor necrosis factor induce hepatic haem oxygenase. Feedback regulation by glucocorticoids," *Biochem. J.* 279(3):891-894 (Nov. 1991).

(Continued)

*Primary Examiner*—Christina Chan
*Assistant Examiner*—Marianne DiBrino
(74) *Attorney, Agent, or Firm*—Dorsey & Whitney LLP.; Todd A. Lorenz

(57) ABSTRACT

Novel oligonucleotides comprising a sequence derived by a computer program are provided for inhibiting cytotoxic activity of lymphocytic cells, inhibiting production of inflammatory cytokines and inflammatory responses associated with those cytokines, inhibiting the activity of heme-containing enzymes and delaying the onset of an autoimmune disease. By combining the subject compositions with mixtures of cells comprising lymphocytic cells and cells which would otherwise activate the lymphocytic cells, lysis of the target cells can be substantially inhibited. The oligopeptides may be joined to a variety of other groups or compounds for varying the activity of the subject composition. The subject compositions may be administered by any convenient means to inhibit lymphocytic attack on tissue, particularly involved with xenogeneic or allogeneic transplants or to inhibit the production of inflammatory cytokines and inflammatory responses associated therewith. The subject compositions may also be used in the inhibition of the activity of heme-containing enzymes.

16 Claims, 2 Drawing Sheets

OTHER PUBLICATIONS

Cuturi, M.C., et al., "Prolongation of allogenic heart graft survival in rats by administration of a peptide (a.a. 75-84) from the α 1 helix of the first domain of HLA-B7 01," *Transplantation* 59(5):661-669 (Mar. 1995).

Dal Porto, J., et al., "A soluble divalent class I major histocompatibility complex molecule inhibits alloreactive T cells at nanomolar concentrations," *Proc. Natl Acad. Sci. USA* 90(14):6671-6675 (Jul. 1993).

Fukuda, Y., et al., "Effect of interleukin-11 on the levels of MRNAs encoding heme oxygenase and haptoglobin in human HepG2 hepatoma cells," *Biochem. Biopphys. Res. Commun.* 193(1):297-302 (1993).

Gao, L., et al., "Both L—and D-isomers of allotrap 2702 prolong cardiac allograft survival in mice," *J. Heart Lung Transplant.* 15(1):78-87 (Jan. 1996).

Grassy, G., et al., "Computer-assited rational design of immunosuppressive compounds," *Nat. Biotechnol.* 16(8):748-752 (Aug. 1998).

Grassy, G., et al., "Variable mapping of structure-activity relationships: application to 17-spirolactone derivatives with mineralocorticoid activity," *J. Mol. Graphics* 13(6):356-367 (Dec. 1995).

Haiech, J., et al., "Use of TSAR as a new tool to analyze the molecular dynamics trajectories of proteins," *J. Mol. Graphics* 13(1):46-48 (Feb. 1995).

Iyer, S., et al., "Characterization and biological significance of immunosuppressive peptide D2702.75-84(E->V) binding protein," *J. Biol. Chem.* 273(5):2692-2697 (Jan. 1998).

Kabat, et al., "Sequences of Proteins of Immunological Interest," NIH publication No. 91-3242, 1:738-740, 770-771, 779-780, 788-789, and 802-804 (1991).

Manolios, N., et al., "T-cell antigen receptor transmembrane peptides modulate T-cell function and T cell-mediated disease," *Nature Med.* 3(1):84-88 (Jan. 1997).

Ngo, et al., "The Protein Folding Problem and Tertiary Structure Prediction," K. Merz, Jr., and S. LeGrand (eds.), Birkhauser: Boston, MA, 491-495 (1994).

Nisco, S., et al., "Induction of Allograft Tolerance in Rats by an HLA Class-I-derived Peptide and Cyclosporine A," *J. Immunol.* 152(8):3786-3792 (Apr. 1994).

Pringle, J.H., (Direct Submission), NCBI Accession No. A38244 (GI2294842), Apr. 14, 1994.

Stagsted, J., et al., "Regulation of insulin receptor functions by a peptide derived from a major histocompatibility complex class I antigen," *Cell* 62(2):297-307 (Jul. 1990).

Tufveson, G., et al., "New immunosuppressants: testing and development in animal models and the clinic: with special reference to DSG," *Immunol. Rev.* 136:99-109 (Dec. 1993).

Viswanadhan, V., et al., "Atomic Physicochemical Parameters for Three Dimensional Structure Directed Quantitative Structure—Activity Relationships. 4. Additional Parameters for Hydrophobic and Dispersive Interactions and Their Application for an Automated Superposition of Certain Naturally Occuring Nucleoside Antibiotics," *J. Chem. Inf. Comput. Sci.* 29(3):163-171 (1989).

Willis, D., et al., "Heme oxygenase: a novel target for the modulation of the inflammatory response," *Nat. Med.* 2(1):87-90 (Jan. 1996).

Yasri, A., et al., "Rational choice of molecular dynamics simulation parameters through the use of the three-dimensional autocorrelation method: application to calmodulin flexibility study," *Protein Eng.* 9(11):959-976 (Nov. 1996).

* cited by examiner

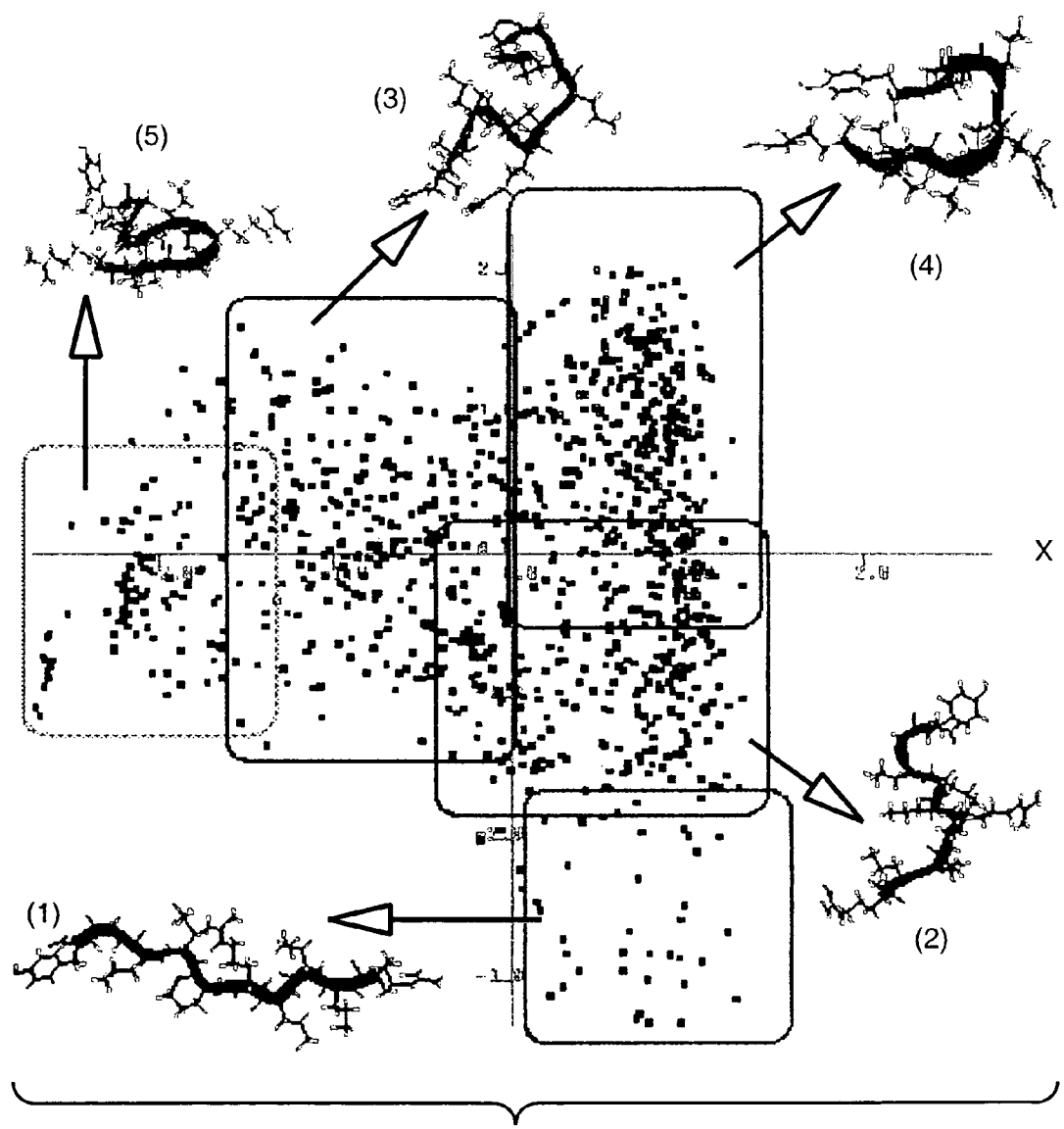
FIG._1

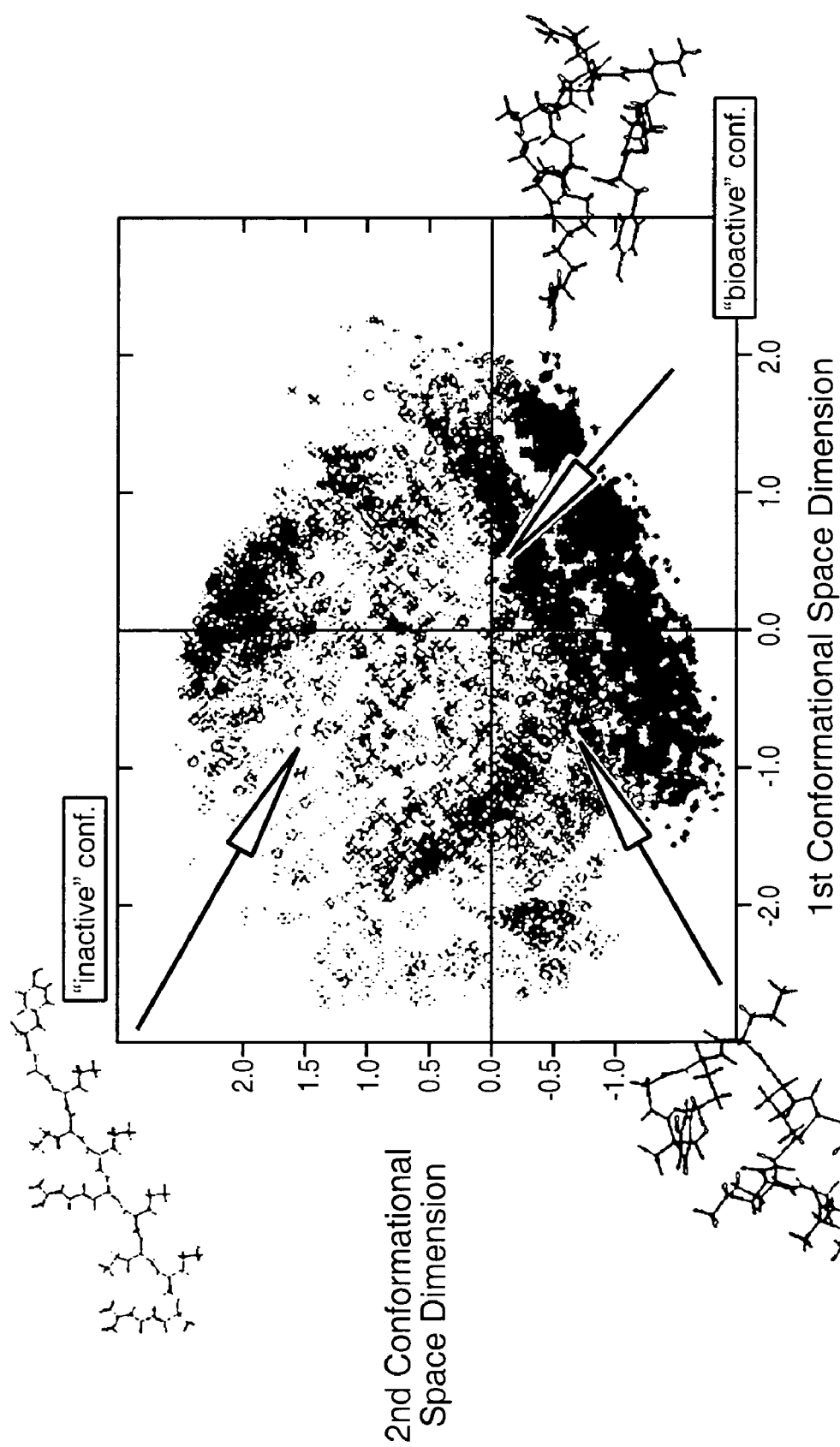
FIG._2

CYTOMODULATING LIPOPHILIC PEPTIDES FOR MODULATING IMMUNE SYSTEM ACTIVITY AND INHIBITING INFLAMMATION

CROSS-REFERENCES TO RELATED APPLICATIONS

This application is a continuation of U.S. application Ser. No. 09/028,083, filed Feb. 23, 1998, now U.S. Pat. No. 6,696,545 which is a continuation-in-part of U.S. application Ser. No. 08/838,916, filed Apr. 11, 1997 now abandoned.

INTRODUCTION

1. Technical Field

The field of this invention is novel peptides useful for modulating the activity of immune system cells and for the inhibition of inflammation.

2. Background

The immune system is an extraordinarily complex combination of cells and compositions that protects a mammalian host against a wide variety of pathogens, while surveiling the body against deleterious aberrations, such as neoplasia. One branch of the immune system involves the cells that carry out immune system functions, including both (a) lymphocytes, such as the bone marrow-derived B-lymphocytes, the thymus-derived T lymphocytes and natural-killer (NK) cells, and (b) the mononuclear phagocytes, including both monocytes and macrophages. While lymphocytes are primarily associated with specific immune responses, due to their ability to specifically recognize and distinguish antigenic determinants, the mononuclear phagocytes are most often involved in the general removal of foreign microbes through phagocytosis as well as the production and secretion of cytokines as induced either directly by a microbe itself or in response to antigen-stimulated T lymphocytes. The functions of lymphocytic cells and the mononuclear phagocytes are highly interconnected and essential for proper immune system function.

One important subset of lymphocytic cells are T lymphocytes, which derive their designation from the fact that they are processed by the thymus. T lymphocytes are a complex group of cells which may be cytotoxic, having numerous mechanisms for inducing cell death, or activating, by secreting various cytokines that function to activate other cells. Cytotoxic T lymphocytes ("CTLs") act by being restricted to a particular major histocompatibility complex (MHC) antigen and express a cell surface T cell receptor which comprises both an α and β chain and which has specific affinity for a particular MHC complex associated with a peptide in the groove of the MHC. CTLs have been screened so that they do not normally act against cells where the peptide in the groove is endogenous to the host. However, where the MHC is foreign or the peptide in the groove is foreign to the host, the CTLs will attack such cell and kill it. Other lymphocytic cells which play important roles in the immune response include B-lymphocytes and natural killer (NK) cells, both of whose activity may be influenced by other cells of the immune system and various cytokine polypeptides.

The mononuclear phagocytes constitute a second major cell population of the immune system and consist of cells having a common lineage whose primary function is phagocytosis. The mononuclear phagocytes derive from progenitor bone marrow stem cells and, after maturation and subsequent activation, can achieve various morphological forms, including incompletely differentiated monocyte cells and macrophages. Proper function of the mononuclear phagocytes is dependent on the ability to both produce and respond to various cytokine proteins.

Cytokines, such as the various interferons, interleukins, tumor necrosis factors, chemokines, hematopoietic growth factors and migration inhibition factors are a diverse group of proteins that are produced by a wide variety of different cells types of the immune system. Most importantly, cytokines are produced and/or responded to by various lymphocytes and mononuclear phagocytes in response to various stimuli. For the most part, cytokines are produced during the effector phases of both natural and specific immunity and serve to mediate and regulate both immune and inflammatory responses. Cytokines, like other polypeptide hormones, initiate their action by binding to specific receptors on the surface of target cells, their activation often resulting in an inflammatory response.

While activation of the immune response and cytokine-induced inflammatory responses are extremely important to a host's health and proper functioning of the immune system, there are a number of situations where such activation is undesired. One particular area is associated with transplantation, where one rarely has an identical match between the donor and recipient of the MHC antigens. Another incidence is where there is a failure on the part of CTLs in that they attack cells where the MHC and associated peptide are both endogenous, as occurs in autoimmune diseases such as insulin-dependent diabetes mellitus (IDDM). An additional incidence is where a cytokine-mediated inflammatory response functions to adversely affect the health of the host, such as inflammatory responses associated with such maladies as septic shock, rheumatoid arthritis, Crohn's disease, colitis, and the like.

Immunosuppression has become a general approach in situations where activation of CTLs is undesired. However, immunosuppressants such as cyclosporin A, FK506, and the like, have numerous undesirable side effects. Additionally, various approaches have been employed for controlling or inhibiting inflammatory responses, however, many of these approaches also have one or more undesirable effects. There is, therefore, substantial interest in identifying new agents which can act to inhibit the activation of lymphocytic cells, particularly CTLs, while having less of a universal immunosuppressive effect on the immune system and fewer side effects, so as to leave the host with a substantial proportion of the immune system for protection against adventitious infection. There is also a substantial interest in identifying new agents that function to control or inhibit adverse inflammatory reactions.

In the last few years, oligopeptides have been reported as being effective in modulating immune system activity and extending the lifetime of allogeneic transplants. These oligopeptides are based on the human leukocyte antigen-B (HLA-B) α1-domain and have a conserved amino acid sequence Arg-X-X-X-Arg-X-X-X-X-Tyr (SEQ ID NO:1), with the various amino acids designated as X varying within a relatively few amino acids to retain activity (e.g., see WO 95/13288). The mechanism by which these oligopeptides effectuate their activity is not understood, particularly as to how they cooperate with subtherapeutic doses of cyclosporin to extend the lifetime of allogeneic transplants.

Also reported (Manolios, NOVEL PEPTIDE, PCT application, filed based on Australian application Nos. PN 0589 and PN 0590, Jan. 16, 1995) as having an effect on T cell mediated inflammation are oligopeptides of the formula:

A-B-C-D-E wherein: A is absent or is 1 or 2 hydrophobic residues; B is a positively charged amino acid; C is a peptide consisting of from 3 to 5 hydrophobic amino acids; D is a positively charged amino acid; and E is absent or is up to 8 hydrophobic amino acids. The peptides that were synthesized are: Gly-Leu-Arg-Ile-Leu-Leu-Leu-Lys-Val (SEQ ID NO:2); Met-Gly-Leu-Arg-Ile-Leu-Leu-Leu (SEQ ID NO:3); Leu-Gly-Ile-Leu-Leu-Leu-Gly-Val (SEQ ID NO:4); Leu-Asp-Ile-Leu-Leu-Leu-Gly-Val (SEQ ID NO:5); Leu-Arg-Ile-Leu-Leu-Leu-Ile-Leu-Val (SEQ ID NO:6); and Leu-Arg-Leu-Leu-Leu-Lys-Val (SEQ ID NO:7). The sequences are predicated on the sequence of a transmembrane sequence of TCR-α. There is no support in this application that the peptides have a beneficial effect on extending transplantation lifetimes.

Relevant Literature

Buelow et al., *Transplantation* 59:649-654 (1995) and references cited therein. Manolios et al., *Nature Medicine* 3:84-88 (1997) describes oligopeptides derived by rational design which modulate T cell activity. WO 95/13288 by Clayberger et al. which describes peptides capable of modulating T cell activity. References describing methods for designing compounds by computer using structure activity relationships include Grassy et al., *J. of Molecular Graphics* 13:356-367 (1995); Haiech et al., *J. of Molecular Graphics* 13:46-48 (1995); Yasri et al., *Protein Engineering* 11: 959-976 (1996) and Ashton et al., *Drug Discovery Today* 1:71-78 (1996).

SUMMARY OF THE INVENTION

Cytomodulating peptides are provided which are capable of (1) modulating the activity of various immune system cells, particularly lymphocytic cells, more particularly CTLs, (2) inhibiting the production of inflammatory cytokines by cells capable of producing such cytokines, thereby being effective in the treatment of conditions associated with adverse inflammatory reactions, (3) modulating the activity of heme-containing enzymes and/or (4) delaying the onset of insulin-dependent diabetes mellitus (IDDM) in a host susceptible of having IDDM, where the peptides are based upon a design in accordance with a computer program. Exemplary of the compounds are oligopeptides comprising the sequence B-X-X-X-B-X-X-X-J-Tyr (SEQ ID NO:8), where B is a basic amino acid, J is Gly, B, or an aliphatic hydrophobic amino acid of from 5-6 carbon atoms and X is any amino acid other than an aliphatic polar amino acid, where at least three Xs are the same aliphatic non-polar amino acid, dimers thereof and D-stereoisomers thereof, and wherein the amino acid sequence may be part of a ring. The peptides find use for inhibiting the activation of immune system lymphocytes, particularly cytotoxic lymphocytes, either by themselves or in conjunction with other immunosuppressant agents, particularly in extending the lifetime of transplants. The peptides described herein also find use for inhibiting the production of inflammatory cytokines (e.g., interferon-γ, IL-1, IL-4, IL-5, IL-6, IL-8, IL-10, IL-12, IL-13, IL-16, MIP1α, etc.), thereby being useful for inhibiting inflammatory responses associated with various disorders such as rheumatoid arthritis, septic shock, Crohn's disease, colitis, allergic reactions, autoimmune diseases, and the like, for inhibiting the activity of heme-based enzymes such as heme oxygenase, nitric oxide synthase, etc., and delaying the onset of IDDM in a patient at risk for developing IDDM, both in vitro and in vivo Administration of the peptides may be ex vivo of an organ to be transplanted or in vivo by any convenient means, including by direct application or administration of the peptide or nucleic acid encoding the desired peptide, in sufficient amount to substantially inhibit lymphocytic activation, inhibit the production of inflammatory cytokines and the associated inflammatory process, inhibit heme-based enzyme activity, an activity that has been previously associated with inflammatory responses and/or delaying the onset of IDDM.

BRIEF DESCRIPTION OF THE DRAWINGS

FIG. 1 is a depiction of the conformational space clustering of the bc1-nL peptide (SEQ ID NO:13). The conformations drawn are obtained from cluster analysis of bc1-nL trajectory.

FIG. 2 is a depiction of a projection of peptide trajectories into the principal plan of D2 peptide (SEQ ID NO:14) reference trajectory.

DESCRIPTION OF THE SPECIFIC EMBODIMENTS

Methods and compositions are provided for modulating the activity of immune system cells, particularly T and B cells and mononuclear phagocytes, more particularly, CTL and NK cell activity, in vitro and in vivo. Also provided are methods and compositions effective for inhibiting the production of inflammatory cytokine(s), thereby finding use for therapeutically treating disorders associated with adverse inflammatory responses, for inhibiting the activity of various heme-based enzymes and/or for delaying the onset of autoimmune diseases such as IDDM. The peptides, having particular effect as CTL and NK cell cytomodulating peptides, are provided in accordance with a computer program, as specified in the description of the Relevant Literature. Following the procedure described in Grassy et al., supra, parameters were defined based on known oligopeptides which have previously been found to have the ability to inhibit T cell activity. See, e.g., Buelow et al., supra. The conformational space necessary for immunosuppressive activity was computed according to the procedure described by Yasri et al., supra.

Using these parameters, compounds having known T cell inhibitory activity were shown to come within these parameters and a number of new peptide compounds were able to be devised and tested. New peptide compounds were found to have activity, equal to or surpassing known active compounds. Known active compounds include HLA-B $\alpha_1$-domain, particularly the amino acids from 75 to 84 and variations of this sequence, where not more than 2 amino acids are replaced, which amino acids do not include R and Y, wherein the present invention is not intended to encompass such known compounds (see, e.g., WO 95/13288 and Buelow et al., supra). Also known are sequences based on the human TCR-α transmembrane region consisting of that sequence and sequences having not more than 2 mutations from that sequence. These sequences include 2 basic amino acids, where the 2 basic amino acids are separated by 4 aliphatic hydrophobic amino acids, although the application indicates that from 3 to 5 hydrophobic amino acids may be present. By mutation is intended each substitution of one amino acid for another or an insertion or deletion, each being counted as one mutation.

In the core sequence of the new peptide compounds described herein, desirably there are two basic amino acids separated by from three to four hydrophobic amino acids, particularly three hydrophobic amino acids, particularly where the N-terminus is a basic amino acid. More desirably, the C-terminal amino acid is an aromatic amino acid, particularly tyrosine. Of particular interest is where at least one of the oligopeptide core terminal amino acids is an oligopeptide terminal amino acid, which may be in the monomeric or oligomeric form of the compound.

New isolated peptide compounds were devised comprising the sequence B-X-X-X-B-X-X-X-J-Tyr (SEQ ID NO:9), where B is a basic amino acid, namely Lys or Arg, particularly Arg at least one position, preferably at both positions, J is Gly, B or an aliphatic hydrophobic amino acid of from 5 to 6 carbon atoms, particularly Gly or B, and X is any amino acid other than an aliphatic charged amino acid, preferably any amino acid other than a polar amino acid, where at least three Xs are the same aliphatic non-polar amino acid, preferably at least 4 are the same aliphatic non-polar amino acid, and more preferably at least all but one are the same aliphatic non-polar amino acid, oligomers, particularly, dimers thereof and D-stereoisomer's thereof and wherein the amino acid sequence may be part of a ring.

Either or both the N- and C-terminus may often be extended by not more than a total of about 100, usually not more than a total of about 30, more usually not more than about 20 amino acids, often not more than about 9 amino acids, where the amino acids will have fewer than 25 number %, more usually fewer than 20%, polar amino acids, more particularly, fewer than 20% which are charged amino acids. In addition, the terminal amino group or carboxyl group of the oligopeptide may be modified by alkylation or acylation to provide esters, amides or substituted amino groups, where the alkyl or acyl group may be of from about 1 to 30, usually 1 to 24, preferably either 1 to 3 or 8 to 24, particularly 12 to 18, carbon atoms.

Also included are oligomers, particularly dimers of the oligopeptides, which may be head to head, tail to tail, or head to tail, there being not more than about 6 repeats of the peptide. In addition, 1 or more of the amino acids may be the D-stereoisomer, up to all of the amino acids.

Also, structurally constrained oligopeptides may be employed, such as cyclic peptides of from about 9 to 50, usually 12 to 36 amino acids, where amino acids other than the specified amino acids may be present as a bridge. In some instances, one may use other than amino acid bridges. By having terminal cysteines, one may form a disulfide bridge to close the ring. Alternative methods for ring formation may be found in Chen et al., *Proc. Natl. Acad. Sci. USA* 89:5872-5876 (1992) and Wu et al., *Protein Engineering* 6:471-478 (1993).

For the purposes of this invention, the amino acids (for the most part natural amino acids or their D-stereoisomers) will be broken down into the following categories:

I. Aliphatic
 (a) non-polar aliphatic:
  Gly, Ala, Val, nL, Ile, Leu
 (b) polar aliphatic:
  (1) uncharged:
   Cys, Met, Ser, Thr, Asn, Gln
  (2) charged:
   Asp, Glu, Lys, Arg 2. Aromatic:
 Phe, His, Trp, Tyr
 wherein Pro may be included in the non-polar aliphatic amino acids, but will normally not be included. "nL" intends norleucine, where the non-polar aliphatic amino acids may be substituted with other isomers.

Of the six amino acids indicated by X in the B-X-X-X-B-X-X-X-J-Tyr (SEQ ID NO: 10) peptide sequence, preferably at least 3 are aliphatic amino acids of from 5 to 6 carbon atoms, more preferably at least 4 are aliphatic amino acids of from 5 to 6 carbon atoms, more particularly 6 carbon atoms. The other amino acids may be other uncharged aliphatic amino acids, particularly non-polar aliphatic amino acids or aromatic amino acids.

The core sequence may be extended in either direction by amino acids, which for the most part will be lipophilic, namely the aliphatic uncharged amino acids, and aromatic amino acids. Also, as indicated previously, one or both, usually one terminus of the oligopeptide, may be substituted with a lipophilic group, usually aliphatic or aralkyl, of from 8 to 36, usually 8 to 24 carbon atoms and fewer than two heteroatoms in the aliphatic chain, the heteroatoms usually being oxygen, nitrogen and sulfur. The chain may be saturated or unsaturated, desirably having not more than 3 sites, usually not more than 2 sites of aliphatic unsaturation. Conveniently, commercially available aliphatic fatty acids, alcohols and amines may be used, such as lauric acid, myristyl alcohol, stearyl amine, etc. The lipophilic groups may be reacted with the appropriate functional group of the oligopeptide in accordance with conventional ways, frequently during the synthesis on a support, depending on the site of attachment of the oligopeptide to the support.

Compositions of particular interest will have the following formula:

Arg-U-X-X-Arg-X-X-X-J-Tyr (SEQ ID NO:11)

wherein all of the symbols have been defined previously except U and U is an uncharged aliphatic amino acid or aromatic amino acid, particularly a non-polar aliphatic amino acid or aromatic amino acid.

The subject sequences find use in a variety of ways. For research purposes, they may be used for analyzing the physiological pathway associated with activation and deactivation of CTLs. One can combine CTLs, particularly CTL cell lines having known peptide targets, in conjunction with the subject peptides, particularly radioactively labeled, in the presence and absence of antigen presenting cells to which the CTLs are restricted. After the lysis by the CTLs, one may then separate the activated CTL cells from quiescent CTL cells by means of the marker CD69, which marker is upregulated in vitro upon activation. Separation can be achieved using a FACS and a fluorescent labeled anti-CD69.

By isolating the most fluorescent cells, e.g., the highest 25%, one then lyses the cells and isolates proteins associated with the subject markers, e.g. chromatography, non-denaturing electrophoresis, or the like. Alternatively, one separates the proteins using electrophoresis and then uses a Western blot or other technique with the labeled peptides to identify proteins with which the subject peptides bind. Instead of a radiolabel, any other type of label may be employed, normally a small organic molecule, such as biotin, a fluorescer, and the like. Where biotin is used, after separation, avidin may be added, where the avidin is labeled with a label as described previously.

One may also compare T cells which have been combined with antigen presenting cells in the presence and the absence of the subject peptides. cDNA libraries may be prepared in each instance and representational differential analysis, subtraction, or the like may be employed to detect the differences in expression between the cells which have been activated in the presence and the absence of the subject peptides. One may also determine whether particular subsets of CTLs respond differently from other subsets to the subject peptides by their expression or lack of expression of one or more proteins, particularly surface membrane proteins. In this way, CTLs may be identified which may be removed by leukophoresis or the like, in order to diminish an unwanted CTL attack on tissue.

It has been reported that peptides of the HLA-B $\alpha_1$ domain bind to hsc70, which is known to serve as a chaperone and bind to a variety of sequences in its role as chaperone.

Depending upon their intended use, particularly for administration to mammalian hosts, the subject peptides may be modified widely to change their distribution in the blood stream, diminish or enhance binding to blood components, enhance the lifetime of a peptide in the blood stream, and the like. The subject peptides may be bound to these other components by linkers which are cleavable or non-cleavable in the physiological environment of the blood. The peptides may be joined at any point of the peptide where a functional group is present, such as hydroxyl, thiol, carboxyl, amino, or the like. Desirably, binding will be at either the N-terminus or the C-terminus.

The peptide may be joined to a wide variety of other oligopeptides or proteins for a variety of purposes. For example, the subject peptides may be covalently linked to an immunogen to produce antibodies to the subject peptides, where the antibodies may serve for identification of other peptides having a comparable conformation. In addition, the antibodies may be used to prepare anti-idiotypic antibodies which may compete with the subject peptides for binding to a target site. These anti-idiotypic antibodies may then be used for identifying proteins to which the subject peptides bind.

Alternatively, the subject peptides may be expressed in conjunction with other peptides or proteins, so as to be a portion of the chain, either internal, or at the N- or C-terminus. By providing for expression of the subject peptides, various post-expression modifications may be achieved. For example, by employing the appropriate coding sequences, one may provide for lipidation, e.g., prenylation or myristoylation. In this situation, the subject peptide will be bound to a lipid group at a terminus, so as to be able to be bound to a lipid membrane, such as a liposome. For administration, liposomes may be used, where drugs may be introduced into the lumen of the liposome, so as to cooperate with the subject peptides in diminishing CTL activation. Thus, immunosuppressants may be included in the lumen, so that the subject peptide and immunosuppressant may act in a localized manner.

The subject peptides may be PEGylated, where the polyethyleneoxy group provides for enhanced lifetime in the blood stream. The subject peptides may also be combined with other proteins, such as the Fc of an IgG isotype, which may be complement binding or not bind complement, or with a toxin, such as ricin, abrin, diphtheria toxin, or the like, particularly the A chain.

One can prepare these compositions by preparing a gene encoding the particular peptide or protein, joined to a DNA sequence encoding for the subject peptide. The gene may be introduced into an appropriate expression vector, there being many expression vectors commercially available, whereby the gene is then expressed in an appropriate host. See, Sambrook et al., Molecular Biology: A Laboratory Manual, Cold Spring Harbor Laboratories, Cold Spring Harbor, N.Y., 1989.

The subject peptides may be prepared by chemical synthesis or by using recombinant techniques, as indicated above. Various commercial synthetic apparatuses are available, for example automated synthesizers by Applied Biosystems Inc., Foster City, Calif., Beckman, etc. By using synthesizers, naturally occurring amino acids may be substituted with unnatural amino acids, particularly D-stereoisomers, side chains having different lengths or functionalities, and the like. For recombinant techniques, one may prepare a nucleic acid sequence which encodes a plurality of the subject peptides in tandem, with an intervening amino acid or sequence, which allows for cleavage to the single peptide or head to tail dimer. Where methionine is absent, one may have an intervening methionine which allows for single amino acid cleavage. Alternatively, one may introduce consensus sequences, which are recognized by particular proteases for enzymatic cleavage. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like. Of particular interest are peptides of at least 2, more usually 3 and not more than about 60 lysine groups, particularly polylysines of from about 4 to 20, usually 6 to 18 lysine units, referred to as MAP, where the subject peptides are bonded to the lysine amino groups, generally at least about 20%, more usually at least about 50%, of available amino groups, to provide a multipeptide product. Thus, one obtains molecules having a plurality of the subject peptides where the orientation of the subject peptides is in the same direction, in effect one has a linking group to provide for tail to tail di- or oligomerization. Alternatively, other naturally occurring or synthetic peptides and proteins may be used to provide a backbone for attachment of the subject peptides at the C terminus.

For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like. Alternatively, one may provide for a wide variety of labels, as described previously, including ligands for binding to antibodies or natural receptors, where the peptides may be bound to a support or, alternatively, to another molecule. As already indicated, subject peptides may bind to hsc70, which allows for isolation and purification of hsc70 from other proteins found in the cell.

The subject peptides may be used for modulating the proliferation and/or activation of CTL and/or NK cells. By combining the subject peptides with lymphocytes, proliferation and/or activation of the CTLs by antigen presenting cells is modulated, generally by at least about 20%, more usually at least 40%, and preferably at least about 60%, based on percent lysis as described in the experimental section. The $IC_{50}$ for lysis will generally be less than about 500 µg/ml, generally less than about 200 µg/ml, and more than about 0.1 µg/ml, usually more than about 1 µg/ml.

The subject compositions can be used in vitro to inhibit lysis by T cells of target antigen presenting cells. Thus, in research where one wishes to maintain mixtures of cells, where CTLs would be activated and kill antigen presenting cells, such as macrophages or B-lymphocytes, or other cells which might serve as target cells, e.g., neoplastic cells, viral infected cells, or the like, the lysis can be inhibited so that the cellular population may be maintained while under investigation.

The subject compositions may also be used ex vivo. In cases of transplantation of organs, particularly solid organs or particular cells, whether xenogeneic or allogeneic, the donor organ may be bathed in a medium comprising the subject peptides. In this way, CTLs present within the implant will be inhibited from participating in graft versus host disease. Also, during the period when the subject peptides remain bound to the implant, the recipient's CTLs will be inhibited from being activated. Generally, the concentration of the peptide will vary in the medium, depending upon the activity of the peptide, the level of inhibition desired, the presence of other compounds affecting CTL activation, and the like. Usually, the concentration will be in the range of about 0.1 to 100 µg/ml, more usually in the range of about 1 to 10 µg/ml. Other immunosuppressants which may be present include cyclosporin A, FK506, antibodies for plasma membrane proteins associated with graft rejection, such as antibodies to CD4, CD8, CD2, LFA-1, ICAM-1, CD28, and the like. Subtherapeutic dosages will be employed, generally when present, not less than about 5% of the normal dosage, and not more than about 75%, usually in the range of about 10 to 60%. Other components of the bathing medium will generally be constituents normally used in an organ preservation solution, e.g., HBSS. The time for the organ to be maintained in the medium will generally be in the range of about 2 to 72 h.

The subject compositions may be also employed in vivo, administrating the subject peptide compositions by any convenient means. The subject compositions may be administered prior to implantation, administration usually beginning not earlier than about 14 days prior to implantation, there preferably being at least one dosage administered within three days of administration. The subject compositions may be administered in the period beginning about 6 h prior to implantation and may be continued on a predetermined schedule thereafter, usually not past 30 days, more usually not past 20 days. However, after implantation, the subject peptide compositions may be administered as needed, depending upon the response of the recipient to the organ or cells. In some situations, the subject compositions may be administered chronically, as long as the implant is present in the host.

Generally, in the case where a peptide composition is administered directly to a host, a bolus of the subject composition that is administered will be in the range of about 0.1-50, more usually from about 1-25 mg/kg, of host. The host may be any mammal including domestic animals, pets, laboratory animals, primates, particularly humans. The amount will generally be adjusted depending upon the half life of the peptide, where the half life will generally be at least one minute, more usually at least about 10 min, desirably in the range of about 10 min to 12 h. Short half-lives are acceptable, so long as efficacy can be achieved with individual dosages or continuous infusion or repetitive dosages. Dosages in the lower portion of the range and even lower dosages may be employed, where the peptide has an enhanced half life or is provided as a depot, such as a slow release composition comprising particles, introduced in a matrix which maintains the peptide over an extended period of time, e.g., a collagen matrix, use of a pump which continuously infuses the peptide over an extended period of time with a substantially continuous rate, or the like.

In addition to administering the subject peptide compositions directly to a cell culture in vitro, to solid organs or particular cells ex vivo or to a mammalian host in vivo, nucleic acid molecules (DNA or RNA) encoding the subject peptides may also be administered thereto, thereby providing an effective source of the subject peptides for the application desired. For the most part, nucleic acid molecules encoding the subject peptides may be cloned into any of a number of well known expression plasmids (see Maniatis et al., supra) and/or viral vectors, preferably adenoviral or retroviral vectors (see, e.g., Jacobs et al., *J. Virol.* 66:2086-2095 (1992), Lowenstein, *Bio/Technology* 12:1075-1079 (1994) and Berkner, *Biotechniques* 6:616-624 (1988)), under the transcriptional regulation of control sequences which function to promote expression of the nucleic acid in the appropriate environment. Such nucleic acid-based vehicles may be administered directly to a transplant tissue ex vivo (e.g., ex vivo viral infection of cells for transplant) or to a desired site in vivo, e.g., by injection, catheter, and the like, or, in the case of viral-based vectors, may be administered systemically. Tissue specific promoters may optionally be employed assuring that the peptide of interest is expressed only in a particular tissue or cell type of choice. Methods for recombinantly preparing such nucleic acid-based vehicles are well known in the art as are techniques for administering nucleic acid-based vehicles for peptide production both in vitro and in vivo.

Transplantation may involve any organ or cells, including organs such as a heart, kidneys, lung, eyes, liver, gut, vascular vessel, or other organ, and cells, such as β-islet cells, bone marrow cells, or other cells, where the organ or cells are allogeneic or xenogeneic, particularly where one or more of the Class I or II MHC antigens are different in the donor as compared to the recipient.

The subject peptides, by themselves or as conjugates, or nucleic acid vehicles encoding such peptides, may be prepared as formulations in pharmaceutically acceptable media, for example, saline, PBS, aqueous ethanol, glucose, propylene glycol, or the like or as solid formulations in appropriate excipients, generally at a pharmacologically effective dose. The concentrations of the peptides or nucleic acid encoding therefore will be determined empirically in accordance with conventional procedures for the particular purpose. The formulations may include bactericidal agents, stabilizers, buffers, or the like. The amount administered to the host will vary depending upon what is being administered, the purpose of the administration, such as prophylaxis or therapy, the state of the host, the manner of administration, the number of administrations and the interval between administrations, and the like, and such may be determined empirically by those skilled in the art. In order to enhance the half life of the subject peptide or subject peptide conjugates, the peptides may be encapsulated, introduced into the lumen of liposomes, prepared as a colloid, or other conventional technique may be employed, which provides an extended life time of the peptides ex vivo or in vivo.

The subject peptides are capable of inhibiting the cellular production of inflammatory cytokines. Inflammatory cytokines inhibited by the peptides of the present invention include, for example, tumor necrosis factors, including tumor necrosis factor-α (TNF-α), interferons, including interferon-γ (INF-γ), interleukin (IL)-1, IL-4, IL-5, IL-6, IL-8, IL-10, IL-12, IL-13, IL-16, MIP1α, chemokines, hematopoietic growth factors, and the like, both in vitro and in vivo. Therefore, the subject peptides will find use in both prophylactic and therapeutic inhibition of inflammatory responses that are associated with a variety of disorders such as septic shock, Crohn's disease, colitis, rheumatoid arthritis and other autoimmune diseases, allergic reactions, atherosclerosis, infection, and numerous other situations where an anti-inflammatory response is desired.

The subject compositions are also capable of modulating the activity of heme-containing enzymes both in vitro and in vivo. As demonstrated below, the subject peptides mimic a porphyrin-like structure that is capable of modulating the activity of heme-containing enzymes such as heme oxygenase (HO), the various isoforms of nitric oxide synthase (NOS), cyclooxygenase, guanylate cyclase, and the like. Therefore, the subject compositions may be used in situations where one wishes to upregulate the expression of a heme-containing enzyme, for example, heme oxygenase. In this regard, heme oxygenase is known to be involved in pathways other than modulation of lymphocytic activity. Therefore, by upregulating the expression of heme oxygenase, those pathways which involve heme oxygenase will be affected. See, e.g., Willis et al., *Nature Medicine* 2:87-89 (1996).

Moreover, heme-containing enzymes such as heme oxygenase are reported to be a factor in the inflammatory response and can have an anti-inflammatory effect. The subject peptides can, therefore, be used in cultures to evaluate the role of heme-containing enzymes in various physiological processes, by comparing the cellular responses in the presence and absence of the subject peptides. The subject peptides may also be used in vivo for reducing the inflammatory response associated with septic shock, Crohn's disease, colitis, including both ulcerative and mucosal colitis, rheumatoid arthritis, atherosclerosis, reperfusion, infection, and the like. The description of the use of the subject peptides for modulating lymphocytic activity is substantially applicable for these indications.

The subject peptides also find use for delaying the onset of an autoimmune disease in a mammalian subject who is at risk of developing such an autoimmune disease. The peptides of the present invention find particular use for delaying the onset of insulin-dependent diabetes mellitus (IDDM), rheumatoid arthritis or systemic lupus erythematosus in a mammal at risk of developing the disease. The description of the use of the subject peptides for modulating lymphocytic activity is substantially applicable for these indications.

The following examples are offered by way of illustration and not by way of limitation.

EXPERIMENTAL

The computer program used to predict and to devise the immunosuppressive activity of peptides and pseudopeptides was developed as follows:

1. Methodology

On the basis of an initial experimental data set made of peptides showing or not showing immunosuppressive activity, there was deduced:

i. A consensus sequence containing the amino acids required for the activity and allowing the development of new peptides or pseudopeptide libraries.

ii. A set of physicochemical and topological properties involved in the activity and converted into a set of constraints by the variable mapping technique (Grassy et al., *J. of Molecular Graphics* 13: 356-367 (1995)).

2. Variable Mapping

The method is based on physicochemical and conformational constraints, as deduced from the results of a training set of data.

Physiochemical Constraints

The method requires the determination of physicochemical constraints defined as ranges of properties for said biological activity. The computational method used for the determination of the set of constraints is named Variable Mapping and is described below.

The Variable Mapping Approach

This qualitative technique consists of an evaluation of the distribution (global or percent wise) of the active and inactive molecules as a function of the values of given parameters. The superposition of all graphs (activity-property) exhibits, for certain parameters, to the limiting values (low and/or higher) which are necessary for leading to an active compound. This graphical method gives a diagnosis of the qualitative non-linear dependencies between the activity and a molecular property. Regarding those properties involved in receptor ligand interactions, it has been clearly established that the existence of strict contingencies determining the adaptability to the receptor imply an embedding of certain structural and physicochemical properties. This method results in simple rules which can be used to predict the activity of unknown products. A graphical representation showing the number of successes relative to the number of violations of the rules allows one to compare the distributions with the activities for the whole set of molecules under study.

3. Physicochemical and Topological Parameters Used in the Definition of the Constraints Involved in the Immunosuppressive Activity of Peptides and Pseudopeptides.

Lipophilicity

Lipophilicity of peptides expressed as log P (where P is the partition coefficient of a named peptide between water and n-octanol). Molecular log P values can be computed by TSAR 2.31 using the atomic incremental log P values determined by Ghose et al., *J. Chem. Inf. Comput.* 29:163 (1989) As demonstrated by the analysis of the initial data set, the lipophilicity of an immunosuppressive peptide must be $\geq -6.85$ Topological Indices Balaban Index (Balaban, *Chem. Phys.* 89:399 (1982))

The Balaban index computed for a connected molecular graph (H suppressed) is calculated as follows:

$$\frac{M}{\mu+1}\Sigma(D_i D_j)^{-0.5}$$

where M is the number of edges in the graph, $\mu$ is the cyclomatic number of the graph, i.e. the minimum number of edges which must be removed before G becomes acyclic, and $D_i = \Sigma D_{ij}$ (with j=1) is a distance matrix of the shortest path between the two vertices.

Molecular Volume

The molecular volume is computed assuming standard Van der Waals radii for each element. This calculation is done on the extended conformation of the peptide.

Ellipsoidal Volume

This volume is computed after determination of the three components of the inertia momentum of the molecule, assuming mean atomic masses for constituent atoms. This calculation is done on the extended conformation of the peptide.

Molar Refractivity

Molar refractivity is computed using the atomic molar refractivity values determined by Ghose et al., supra.

Dipole Moment

This parameter is computed on the extended conformation of the peptides. The total dipole moment for a molecule is expressed in Debye units.

$$\mu = e\Sigma r_i q_i$$

where $r_i$ is the distance of an atom i to the origin, $q_i$ is the charge of the atom i. The charges on the atoms are computed using the Charge-2 method. (Abraham and Smith, *J. Comput. Aided Mol. Design.* 3:175-187 (1989))

Kier Chir V 4

This index is one of the connectivity indexes developed by L. B. Kier. The Kier Chi V 4 computes in several steps (H included).

a. Determination and numbering of all the paths of length 4 on the molecular graph of the peptide.

b. Computation of each path of length 4 of the following quantities:

$$c_s^v = \Pi[(\partial_j^v)]^{-0.5}$$

j=1, 4, where $\delta_i = Z_i - h_i$ is defined for an atom as the difference between the total number of valence electrons $Z_i$ and the number $h_i$ of hydrogen atoms bonded to the atom i.

c. Summation of all these values concerning the entire set of subgraphs of length 4 on the graph $$\chi = \Sigma(c_v^s)$$

Kier Kappa Alpha

Kier Kappa Alpha 1 ($K\alpha^1$)

If A is the total number of atoms of the molecule (H included), $K\alpha^1$ is equal to:

$$\frac{(A+\alpha)(A+\alpha-1)^2}{(P_1+\alpha)^2}$$

with:

$$\alpha_i = \frac{r_i}{rC_{sp^3}} - 1$$

$r_i$ is the covalent radius of the atom i and $rC_{sp}^3$ the covalent radius of a carbon sp3, $P_1$ is the total number of paths of length=1 along the molecular graph of the peptide under study.

Kier Kappa Alpha 2 ($K\alpha^2$)

If A is the total number of atoms of the molecule (H included), $K\alpha^2$ is equal to:

$$\frac{(A+\alpha-1)(A+\alpha-2)^2}{(P_2+\alpha)^2}$$

with:

$$\alpha_i = \frac{r_i}{rC_{sp^3}} - 1$$

$r_i$ is the covalent radius of the atom i and $rC_{sp}^3$ the covalent radius of a carbon $sp^3$, $P_2$ is the total number of paths of length=2 along the molecular graph of the peptide under study.

Flexibility Phi

Based upon the above formulas, the flexibility of a molecule can be defined as:

$$Phi = (K\alpha^1)(K\alpha^2)/A$$

where A is the total number of atoms (H included).

Atoms and Groups Counts:

The number of the following atom types was also used as a constraint:

Total number of oxygen atoms of the peptide
Total number of nitrogen atoms of the peptide The number of the following groups was also used as a constraint:

Total number of ethyl groups
Total number of hydroxyl groups

4. Values of the Constraints

Generation of Peptide or Pseudopeptide Libraries

Starting from the consensus sequence Arg-X-X-X-Arg-X-X-X-X-Tyr (SEQ ID NO:1) where X is an amino acid which is as defined in the earlier analogous formula, the physicochemical and topological parameters previously described were computed and whether these parameters were within the constraints defined by the initial training set. For example, starting from X=Leu, nLeu, Trp, Tyr, Gly or Val, a library of 279,936 molecules was generated and only 26 of them satisfied the required constraints.

The ranges of properties necessary to obtain a biological activity are summarized in the following Table I.

TABLE I

Value ranges of physicochemical and structural parameters

| Property | Minimum | Maximum |
|---|---|---|
| LogP | −6.849 | −0.004 |
| Ellipsoidal Volume | 5785.5 | 29460.00 |
| Molecular Volume | 660.9 | 1050.4 |
| Molar refractivity | 221.30 | 359.3 |
| Kier Chi V4 | 3.325 | 5.342 |
| Kappa $\alpha_2$ | 26.120 | 44.31 |
| Flexibility | 22.50 | 40.3 |
| Balaban Index | 2.846 | 6.701 |
| Total Dipole | 3.423 | 80.79 |
| Number of oxygen atoms | 10 | 15 |
| Number of nitrogen atoms | 8 | 20 |
| Number of ethyl groups | 0 | 1 |
| Number of hydroxyl groups | 1 | 3 |

5. Characterization of the Conformational Space Involved in the Immunosuppressive Activity of Peptides and Pseudopeptides.

Spatial Autocorrelation Vector of a 3D Structure

The concept of autocorrelation description of a molecular structure was first introduced by Broto et al., *Eur. J. Med. Chem.* 19:66-70 (1984)). This vector basically represents the discretized distance distribution derived from the interatomic distance matrix of a molecule. The first component of this vector ($A_o$) is equal to the number of atoms of the structures, the other components, $A_1 \ldots A_n$, are defined by the number of atom pairs which are separated by a distance within the range defined by a lower limit $(n-1)D_i$, where n is the order of the bin of the vector and $D_i$ the distance increment. Similarly, it is possible to calculate the distribution of an atomic property P. In this case, the weighted autocorrelation component $AP_n$ is obtained by the sum of the products of property values P on atoms i, j, having an interdistance belonging to the distance interval [$(n-1)D_i$, $nD_i$]. The number of components of the vector is then defined by $n_{max}=(D_{max}/D_i)+1$, where $D_{max}$ is the greatest interatomic distance in the structure.

The autocorrelation vector exhibits some useful features:

This vector achieves a substantial reduction of conformational data. An entire conformation is described by a limited set of n numerical values.

The vector is very easy to calculate on the basis of 3D coordinate data. Therefore, it is possible to compute and store this vector during molecular dynamics simulations, the reduction of the size of the storage involved in such a process, in comparison to the classical storage of a set of complete distance matrices, allows much longer simulations than usual.

The autocorrelation vector of a conformation is transitionally and rotationally invariant and is also independent of the atomic numbering of the molecule.

This vector is sensitive both to minor and major changes in conformation: the more the conformation is changed, the more the components of the vector are modified. The sensitivity depends on the distance increment chosen for calculations, but an increment from 0.5 Å or 1 Å (small molecules) to 5 Å (macromolecules) is a good choice for the usual simulations (Yasri et al., Protein Engineering 11:959-976 (1996)).

It is possible to analyze only a part of a structure or only a specific subset of atoms of this structure, e.g. $C_\alpha$ in proteins, N atoms, heavy atoms, etc. The vector is entirely defined by the knowledge of a structure, so that the comparison of different structures can be performed, using this vector without any reference.

Molecular Dynamics Analysis Using 3-D Autocorrelation Vectors

Applied to HLA-B2702.75-84 peptide (amino acid sequence Arg-Glu-Asn-Leu-Arg-Ile-Ala-Leu-Arg-Tyr) (SEQ ID NO:12) and on various active and inactive derivative peptides thereof molecular dynamics simulations were performed using AMBER 4.1. The simulation of one nanosecond of dynamics generate a set of $10^3$ conformations (one conformation pet picosecond). For each conformation the 3D autocorrelation vector was calculated using TSAR with a distance increment of 1 Å and the entire set of conformations was stored as 3D autocorrelation vectors versus time matrix ($10^3$xn).

The aim of the work was to define the conformational space responsible for immunosuppressive activity, by comparison of the conformational spaces of active and inactive peptides using the methodology explained in the references cited in the Relevant Literature.

Statistical Analysis

Cluster Analysis

In order to compare different conformations, the distance matrix between all of these conformations in the hyperspace defined by the components of their unweighted 3D autocorrelation vectors was determined. The more the structure of two compounds are analogous, the shorter their distance. This method provides a quantification of the rigid molecular fit. Using the starting conformation as a reference, the numerical value of this distance is analogous to a root-mean-square deviation.

Principal Component Analysis (PCA)

PCA is a multidimensional statistical method for data analysis, suited for representing molecules in the hyperspace of their properties (molecular descriptors). PCA can be used to reduce a large number of descriptors to a smaller number of synthetic orthogonal variables issued from a linear combination of the original descriptors. This method retains the largest part of the total initial information. The original variables were normalized and the diagonalization of the covariance matrix was calculated using the classical Jacobi transform routine. The components of the 3K autocorrelogram vector provide a good description of the 3K structure of different conformations, but are awkward to handle because they contain too many data to get an easy visualization. PCA can reduce the dimensionality of the data to a 2D or 3D representation that contains as much of the original information as possible. Using PCA, the immunosuppressive peptides exhibit a well defined common conformational space. All the peptides able to reach these conformational specifications can exhibit an immunosuppressive activity.

Conformational Space Coordinates of Peptide bc1-nL Bioactive Conformation

FIG. 1 shows the two-dimensional conformational space and related conformations of peptide bc1-nL, wherein the bc1-nL peptide has the amino acid sequence Arg-nL-nL-nL-Arg-nL-nL-nL-Gly-Tyr (SEQ ID NO:13) and wherein "nL" is norleucine (see below). The structures drawn were obtained by applying cluster analysis method on the whole trajectory of peptide bc1-N1.

Main Conformations of Peptide bc1-nL

Structural properties of the main visited conformations of bc1-nL (FIGS. 1, (1), (2), (3), (4) and (5)) in its conformational space are summarized in Table II. These properties concern the coordinates in the three dimensional space defined by the three first principal components (PCA coordinates), and the radius of gyration (Rg).

TABLE II

Spatial coordinates (PCA coordinates) and radius of gyration (Rg) of dynamic conformations of peptide bcl-nL.

| | PCA Coordinates | | | |
|---|---|---|---|---|
| Conformations | PC1 | PC2 | PC3 | Rg |
| (1) | 0.785 | −2.816 | −0.531 | 9.92 |
| (2) | 0.382 | −0.899 | −0.164 | 7.99 |
| (3) | −0.811 | 0.345 | −0.481 | 6.93 |
| (4) | 0.741 | 0.950 | −1.092 | 6.76 |
| (5) | −2.096 | −0.296 | 0.770 | 6.67 |

Conformational Space of Active Peptides

The trajectory of the D2 (amino acid sequence Arg-Val-Asn-Leu-Arg-Ile-Ala-Leu-Arg-Tyr) (SEQ ID NO:14) peptide has been described by the 3-D autocorrelation method and the data analyzed by principal component analysis. This provided a principal plan defined by the 2 first principal components which contain all the conformations visited during the trajectory. The D2 peptide trajectory was used as a trajectory reference and all the trajectories calculated were projected into its principal plan (FIG. 2)

The immunosuppressive peptides exhibit a well defined common conformational space featuring the following points:

PCA dimensions:
  PC1: minimum=−2.0; maximum=2.0
  PC2: minimum=−2.0; maximum=1.0
  PC3: minimum=−1.0; maximum=1.0

The following peptides were prepared as compositions

| bc # | | | | | | | | | | SEQ ID NO |
|---|---|---|---|---|---|---|---|---|---|---|
| 1 | Arg | Leu | Leu | Leu | Arg | Leu | Leu | Leu | Gly | Tyr | SEQ ID NO:15 |
| 2 | Arg | Val | Leu | Leu | Arg | Leu | Leu | Leu | Gly | Tyr | SEQ ID NO:16 |
| 3 | Arg | Ile | Leu | Leu | Arg | Leu | Leu | Leu | Gly | Tyr | SEQ ID NO:17 |
| 4 | Arg | Leu | Val | Leu | Arg | Leu | Leu | Leu | Gly | Tyr | SEQ ID NO:18 |
| 5 | Arg | Leu | Ile | Leu | Arg | Leu | Leu | Leu | Gly | Tyr | SEQ ID NO:19 |
| 6 | Arg | Leu | Leu | Val | Arg | Leu | Leu | Leu | Gly | Tyr | SEQ ID NO:20 |
| 7 | Arg | Leu | Leu | Ile | Arg | Leu | Leu | Leu | Gly | Tyr | SEQ ID NO:21 |
| 8 | Arg | Leu | Leu | Leu | Arg | Val | Leu | Leu | Gly | Tyr | SEQ ID NO:22 |
| 9 | Arg | Leu | Leu | Leu | Arg | Ile | Leu | Leu | Gly | Tyr | SEQ ID NO:23 |
| 10 | Arg | Leu | Leu | Leu | Arg | Leu | Val | Leu | Gly | Tyr | SEQ ID NO:24 |
| 11 | Arg | Leu | Leu | Leu | Arg | Leu | Ile | Leu | Gly | Tyr | SEQ ID NO:25 |
| 12 | Arg | Leu | Leu | Leu | Arg | Leu | Leu | Val | Gly | Tyr | SEQ ID NO:26 |
| 13 | Arg | Leu | Leu | Leu | Arg | Leu | Leu | Ile | Gly | Tyr | SEQ ID NO:27 |
| 14 | Arg | Trp | Leu | Leu | Arg | Leu | Leu | Leu | Gly | Tyr | SEQ ID NO:28 |
| 15 | Arg | Leu | Trp | Leu | Arg | Leu | Leu | Leu | Gly | Tyr | SEQ ID NO:29 |
| 16 | Arg | Leu | Leu | Trp | Arg | Leu | Leu | Leu | Gly | Tyr | SEQ ID NO:30 |
| 17 | Arg | Leu | Leu | Leu | Arg | Trp | Leu | Leu | Gly | Tyr | SEQ ID NO:31 |
| 18 | Arg | Leu | Leu | Leu | Arg | Leu | Trp | Leu | Gly | Tyr | SEQ ID NO:32 |
| 19 | Arg | Leu | Leu | Leu | Arg | Leu | Leu | Trp | Gly | Tyr | SEQ ID NO:33 |
| 20 | Arg | Tyr | Leu | Leu | Arg | Leu | Leu | Leu | Gly | Tyr | SEQ ID NO:34 |
| 21 | Arg | Leu | Tyr | Leu | Arg | Leu | Leu | Leu | Gly | Tyr | SEQ ID NO:35 |
| 22 | Arg | Leu | Leu | Tyr | Arg | Leu | Leu | Leu | Gly | Tyr | SEQ ID NO:36 |
| 23 | Arg | Leu | Leu | Leu | Arg | Tyr | Leu | Leu | Gly | Tyr | SEQ ID NO:37 |
| 24 | Arg | Leu | Leu | Leu | Arg | Leu | Tyr | Leu | Gly | Tyr | SEQ ID NO:38 |
| 25 | Arg | Leu | Leu | Leu | Arg | Leu | Leu | Tyr | Gly | Tyr | SEQ ID NO:39 |
| 1nL | Arg | nL | nL | nL | Arg | nL | nL | nL | Gly | Tyr | SEQ ID NO:13 | nL = norleucine

EXAMPLE 1—ANTIPROLIFERATIVE ACTIVITY OF BC PEPTIDES

Adult 6-8 week old male C57BL6/J (B6, H-$2^d$), Balb/c (H-$2^d$) and CBA/J (H-$2^k$) mice were purchased from the Jackson Laboratory, Bar Harbor, Me. They were kept and maintained in the animal facility in the SangStat Medical Corporation according to NIH guidelines and regulations of the Department of Health.

Peptides were synthesized at synt:em (Nimes, France) using an automated peptide synthesizer and Fmoc chemistry. All peptides were synthesized as amides and then converted to acetate salts. Peptides were purified by preparative reverse phase HPLC and shown to be >95% homogenous by analytical reverse phase HPLC. Amino acid content was confirmed by amino acid analysis. Before use, peptides were first dissolved in 1 volume of DMSO (Sigma) followed by addition of 99 volume of culture medium. The final concentration of DMSO in culture was not greater than 0.25%.

Spleen cell suspensions were prepared following lysis of red blood cells by hypotonic shock. Cells were then washed in culture medium and finally resuspended in RPMI-1640 with 10% FBS (R-10 medium) or in serum-free AIM-V medium (Gibco, Grand Island, N.Y.).

Spleen cells isolated from CBA mice were then stimulated ($2 \times 10^5$/well) with anti-CD3 monoclonal antibody (Pharmingen, San Diego) at a final concentration of 0.1 to 1 μg/ml in 96-well, round-bottom microculture plates (Nunc, Denmark). bc peptides at various concentrations were added at the beginning of the culture. Cells were incubated for a period of 3 days at 37° C., 5% $CO_2$. Twenty-four hours before harvesting, 1 μCi[$^3$H]-TdR (Amersham, Arlington Heights, Ill.) was added to individual wells. Cells were then harvested using a Filtermate 196 Harvester (Packard, Downers Grove, Ill.) and the degree of thymidine incorporation was measured using a TopCount Microplate Scintillation Counter (Packard).

The results obtained from these studies demonstrated that while a PBS/DMSO solution lacking peptide and a control peptide 2705 (amino acid sequence Arg-Glu-Asp-Leu-Arg-Thr-Leu-Leu-Arg-Tyr) (SEQ ID NO:40) had no effect on T-cell proliferation, bc peptides inhibited T-cell proliferation between 35% and 75%. These data, therefore, demonstrate that bc peptides exhibit remarkable abilities to inhibit T-cell proliferation.

EXAMPLE 2—EFFECT OF BC PEPTIDES ON CYTOTOXIC T-CELL ACTIVITY

To assay the effect of peptides on cytotoxic T cell activity, CBA to B6 effector cells were prepared following a 6-day culture of $4 \times 10^6$ CBA spleen cells with $5 \times 10^6$ mitomycin-treated B6 spleen cells in wells of a 24 well plate (Nuncion Delta, Nunc, Denmark) in RPMI-1640 with 10% FBS. Effector cells were then harvested and washed. EL4 (H-$2^b$), a mouse lymphoma induced in C57BL/6N was used as target cells. Cultured EL4 cells were maintained and sub-cultured once every three days ($^{51}$Cr) in 20 μl for 1 hour at 37° C. Effector (E) and target (T) cells were then added into V-shaped tissue culture plates (Nunc, Denmark) at E:T ratios of 3:1, 10:1, 30:1, 100:1, respectively. Peptides were diluted to the working concentrations with R-10 medium and added at the beginning of the 4-hour incubation period. For the determination of maximal release, 1% Triton X-100 was added to separate wells. Plates were then centrifuged for 2 min. to increase cellular contact before the 4-hour incubation period. After incubation, 75 µl supernatant from each well was collected and the amount of $^{51}$Cr was counted using a TopCount Scintillation Counter. The degree of cell lysis was calculated using the formula below:

$$\% \text{ Lysis} = \frac{CPM_{Experimental} - CPM_{Spontaneous}}{CPM_{Total} - CPM_{Spontaneous}}$$

The results obtained from these analyses demonstrated that control peptide 2705 at concentrations up to 100 µg/ml had no effect on T-cell mediated target cell lysis, whereas bc peptides inhibited cell mediated lysis in a dose dependent manner. Half-maximal inhibition of CTL activity by bc peptides was observed at about 0.5 µg/ml.

EXAMPLE 3—EFFECT OF BC PEPTIDES ON ALLOGRAFT TRANSPLANTS IN VIVO

The immunosuppressive activity of the bc peptides was evaluated in a vascularized fully mismatched mouse heart allograft model. Specifically, abdominal heterotopic heart transplantation was performed as described previously by Ono and Lindsey, *J. Thoracic Cardiovasc. Surg.* 7:225 (1969)). CBA mice recipients of C57Bl/6 hearts were treated daily with various doses of peptide following organ transplantation. Peptides were dissolved in DMSO and diluted in PBS (final DMSO concentration was 10%) before intraperitoneal administration. Animals were treated starting at the day of transplantation until day five or nine. Graft survival was monitored daily by direct palpation, and rejection was defined as termination of palpable cardiac contractility. The statistical significance of prolongation of heart allograft survival was calculated using the Mann-Whitney test.

The results of these analyses demonstrated that control peptide 2702.75-84 (amino acid sequence Arg-Glu-Asn-Leu-Arg-Ile-Ala-Leu-Arg-Tyr) (SEQ ID NO:41) administered at 80 mg/kg/day (days 0-9) prolonged heart allograft survival to 107±26 days, compared to 8±1.4 days in control animals treated with PBS/DMSO (p<0.01). Administration of control peptide 2702.75-84 at 40 mg/kg/day had no observable effect on transplant survival over the control treatment. In contrast, however, administration of be peptides as low as 1 mg/kg/day resulted in a significant prolongation of heart allograft survival with 50% of the grafts surviving for more than 28 days. These results demonstrate, therefore, that be peptides have immunosuppressive activities sufficient to enhance survival of transplants in mammals.

EXAMPLE 4—ABILITY OF BC PEPTIDES TO BIND TO HSC70

To determine if bc peptides are capable of binding to hsc70, protein binding assays were performed. Specifically, peptide 2702.75-84 was synthesized in a biotinylated form with biotin attached to the N-terminus via a six carbon spacer. ELISA plates (Nunc Maxisorb, Nunc, USA) were coated with 100 ng/ml of recombinant hsc70 (Stressgen, Victoria, Canada) in 100 mM Na-citrate buffer, pH 4.0 overnight at 4° C. Subsequently, remaining binding sites were blocked by incubating the plates with PBS/0.1% Tween 20 (PBS/Tween; Sigma) for 2 hours at room temperature. Unbound material was removed by washing the plates three times with PBS/Tween. Following the addition of biotinylated 2702.75-84 in PBS/Tween/1% DMSO, the plates were incubated for 2 hours at room temperature, washed three times, incubated with 0.1 µg/ml streptavidin conjugated to horseradish peroxidase (streptavidin-HRP) (Jackson ImmunoResearch Laboratories, West Grove, Pa.) and washed again. Bound streptavidin-HRP was detected using 3 mg/ml o-phenylenediamine (OPD; Sigma) in substrate buffer (SangStat, Menlo Park, Calif.). The reaction was stopped by addition of 1 M HCl and absorbance (OD490-OD605) was measured using an ELISA plate reader. Binding of unlabeled peptide was measured in a competition assay. Biotinylated-2702.75-84 (3 µM) was mixed with various amounts of unlabeled bc peptide and then incubated in hsc70 coated plates for 3 hrs at room temperature. Bound biotinylated-2702.75-84 was then detected as described above.

The results of these experiments demonstrated that affinity chromatography using the 2702.84-75-75-84 peptide (inverted dimer) resulted in the purification of hsc70 and hsp70. Upon incubation of hsc70 coated ELISA plates with biotinylated-2702.75-84, we observed a dose dependent binding of this peptide to hsc70. Binding of biotinylated-2702.75-84 to hsc70 could be inhibited by addition of increasing concentrations of 2702.75-84. Half maximal inhibition ($IC_{50}$) was observed at 7.0±3.0 µM. a similar $IC_{50}$ was observed for the bc peptides ($IC_{50}$=2.5–10 µM), thereby evidencing that bc peptides effectively bind to hsc70.

EXAMPLE 5—EFFECT OF BC PEPTIDES ON HEME OXYGENASE AND OTHER HEME ENZYMES

The effect of the bc peptides on hsp32 (heme oxygenase) was evaluated by measuring heme oxygenase (HO) in the presence or absence of bc peptides. Specifically, mouse spleen samples were homogenized on ice in a Tris-Cl lysis buffer (pH 7.4) containing 0.5% Triton X-100 and protease inhibitors. Samples were frozen in small aliquots until use. Spleen homogenates were used as the source of HO for all activity measurements. Biliverdin reductase was purified from rat liver by the method described by Kutty and Maines, *J. Biol. Chem.*, 256:3956 (1981). HO activity was measured by mixing 100 µl of spleen homogenate with 0.8 mM NADPH, 0.8 mM glucose-6-phosphate, 1.0 unit G-6-P dehydrogenase, 1 mM $MgCl_2$ and 10 µl of biliverdin reductase at 4° C. The reaction was initiated by the addition of Hemin (20 µl of 2.5 mM). The reaction mixture was incubated at 37° C. in the dark for 30 min. At the end of the incubation period, any insoluble material was centrifuged and supernatants were analyzed for bilirubin concentration by a modified procedure of Hillman and Beyer, *Z. Klin. Chem.* 5:92 (1981) (Sigma Diagnostics, kit #552). Controls included spleen samples in the absence of the NADPH generating system and all components of the reaction mixture in the absence of the spleen homogenates.

The results of these experiments demonstrated that compared to the inactive control peptide 2705.75-84, bc peptides (100 µg/ml) inhibited HO activity by more than 50%. Thus, bc peptides are capable of inhibiting heme oxygenase activity.

Since bc peptides were determined to effectively inhibit the activity of heme oxygenase, the effect of bc peptides on other heme enzymes such as nitric oxide synthase (NOS) was determined. Specifically, bc peptides and control 2702 peptide were analyzed in enzyme activity assays for the ability to inhibit three different NOS isoforms (neuronal NOS, endothelial NOS and cytokine-inducible NOS) in vitro. The results from these experiments demonstrated that bc peptides were capable of inhibiting NOS with $IC_{50}$ significantly less than that of the control 2702 peptide. Thus, it appears that bc peptides mimic a porphyrin-like structure that particularly influences the activity of heme-containing enzymes and such has been confirmed using computer modeling.

EXAMPLE 6—BC PEPTIDE-MEDIATED INHIBITION OF THE PRODUCTION OF INFLAMMATORY CYTOKINES

In order to determine the effect of bc peptides on the production of inflammatory cytokines, RAW264.7 macrophage cells were stimulated in culture with 10 μg/ml bacterial lipopolysaccharide (LPS) to produce the inflammatory cytokine tumor necrosis factor-α (TNF-α) (see Alleva et al., *J. Immunol.* 153:1674 (1994) and Tonetti et al., *Biochem. Biophys. Res. Comm.* 230:636-640 (1997)), either in the absence or presence (1 to 100 μM) of test peptide. Following incubation for 24 hours, the amount of TNF-α in the culture supernatants was determined by ELISA. Without the addition of LPS, RAW264.7 cells did not produce detectable amounts of TNF-α.

The results from these experiments demonstrated that while the control peptide D2RP (amino acid sequence Arg-Val-Asn-Leu-Pro-Ile-Ala-Leu-Arg-Tyr) (SEQ ID NO:42) showed no ability to inhibit the production of TNF-α by RAW264.7 macrophage cells, be peptides inhibited the production of INF-α in a dose dependent manner. Thus, be peptides will find use in inhibiting the production of inflammatory cytokines, thereby having beneficial utility in the treatment of inflammation and inflammation-associated disorders.

EXAMPLE 7—THE EFFECT OF BC PEPTIDES FOR THE TREATMENT OF AN ANIMAL MODEL FOR SEPTIC SHOCK

Administration of LPS to mice provides an accepted animal model for septic shock (see Otterbein et al., *Amer. J. Physiol.* 272(2):1 (1997), Albrecht et al., *Hepatology* 26:1553-1559 (1997), Haziot et al., *J. Immunol.* 154:6529-6532 (1995) and Otterbein et al., *Am. J. Respir. Cell Mol. Biol.* 13:595-601 (1995)). To provide further evidence of the utility of bc peptides for the treatment of inflammatory responses and inflammatory conditions (such as septic shock), we tested the effect of bc peptides on the survival of mice following administration of LPS thereto. Specifically, mice were treated with 20 mg/kg of control peptide 2705 or bc peptide in mannitol or with mannitol alone. Sixteen hours after administration of the peptide in mannitol or mannitol alone, the mice were injected with 100 mg/kg LPS and survival of the mice was monitored twice daily.

The results of these experiments demonstrated that while all of the mice treated with control peptide 2705 in mannitol or with mannitol alone died on day one after administration of the LPS, more than 50% of the mice treated with bc peptides were alive on day 2 following administration of the LPS and more than 25% of the mice treated with bc peptides were alive on day 3 following administration of the LPS. Thus, these data demonstrate that bc peptides are effective for treating inflammatory conditions such as septic shock.

EXAMPLE 8—ADMINISTRATION OF BC PEPTIDES BY GENE TRANSFER IN VIVO ENHANCES THE SURVIVAL OF MURINE HETEROTOPIC CARDIAC TRANSPLANTS

We next sought to determine if local delivery of bc peptides via plasmid-mediated gene transfer could extend in vivo transplant survival in a murine heterotopic cardiac transplant model. Specifically, C57BL/6 donor neonatal hearts were transplanted subcutaneously into the ear pinnae of CBA/J recipient mice. bc peptide, or 20 μg of plasmid DNA encoding the bc peptide of interest, was injected directly into the allograft at the time of transplantation. Survival of the allografts was determined by electrocardiogram monitoring and rejection was determined as the cessation of cardiac electrical activity. Graft survival is expressed in days (mean ±SEM). Statistical significance was determined by an unpaired Student's t-test.

Direct injection of 1 μg of control peptide 2702 into the allograft did not prolong survival (13.3±0.75 versus 13.9±0.9 for untreated controls) but injection of 400 μg of 2702 peptide did extend survival (22.0±0.58). Injection of 20 μg of plasmid DNA encoding the control 2702 peptide further extended graft survival to 30.3±1.03. Similar results were obtained using another plasmid encoding the bc1 peptide (29.0±4.08), while no significant prolongation was observed using a plasmid encoding the control peptide 2705, which has no immunomodulatory activity in vitro or in vivo (16.5±0.96).

These results demonstrate that in vivo transfer of genes encoding bc peptides is an effective means for delivering bc peptides for therapeutic purposes.

EXAMPLE 9—THE EFFECT OF BC PEPTIDES FOR DELAYING THE ONSET OF INSULIN-DEPENDENT DIABETES MELLITUS (IDDM)

Since the peptides of the subject invention are shown herein to be immunomodulating, we next sought to determine if bc peptides exhibited efficacy for inhibiting the onset of an autoimmune disease in vivo. As a model for autoimmune diseases in general, we have herein determined the ability of bc peptides to delay or inhibit the onset of IDDM in vivo. Specifically, 20 mg/kg of bc peptide was administered intraperitoneally to 6 week old female non-obese diabetic (NOD) mice wherein control mice were either left untreated or were treated with an inactive peptide compound. The above treatments were repeated weekly. Blood glucose levels in the test animals were measured once per week. The onset of IDDM in the test animals was defined as having a blood glucose level of greater than 200 mg/dL.

The results of the above experiments demonstrated that 70 to 80% of the untreated control NOD mice developed IDDM by the age of 22 weeks. No difference was observed in the groups of control animals who were either untreated or treated with an inactive control peptide. However, in the animals treated with bc peptides, only one animal developed IDDM by week 16 and all other test animals had not developed IDDM at 24 weeks. These results, therefore, demonstrate that administration of bc peptides is effective for delaying the onset of IDDM in vivo.

It is evident from the above results, that the subject compositions and methodologies provide for substantial inhibition of cytotoxicity of CTLs. Surprisingly, the subject peptides provide for substantially increased effectiveness in inhibiting lysis as compared to earlier oligopeptides. The use of the subject compositions provides for substantial advantages in requiring lower amounts of the oligopeptide for therapeutic levels, and in inhibiting heme oxygenase activity.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An oligopeptide consisting of the amino acid sequence: Arg-nL-nL-nL-Arg-nL-nL-nL-Gly-Tyr, wherein one or more of the amino acids of said oligopeptide, other than glycine, are optionally D isomers, and wherein the amino acid residue at least one terminus of said oligopeptide is optionally modified.

2. The oligopeptide according to claim 1, wherein all the amino acids of said oligopeptide, other than glycine, are D isomers.

3. The oligopeptide according to claim 1, wherein the terminal carboxyl group of said oligopeptide is amidated.

4. The oligopeptide according to claim 1, wherein said oligopeptide is in salt form.

5. The oligopeptide according to claim 1, wherein the terminal carboxyl group of said oligopeptide is the acetate salt of an amide.

6. An oligopeptide consisting of the structural formula:
H-(D)Arg-(D)nL-(D)nL-(D)nL-(D)Arg-(D)nL-(D)nL-(D)nL-Gly-(D)Tyr-NH$_2$, wherein the amino acid residue at least one terminus of said oligopeptide is optionally modified.

7. An oligopeptide according to claim 6, where said oligopeptide is in salt form.

8. The oligopeptide according to claim 2, wherein the terminal carboxyl group of said oligopeptide is amidated.

9. The oligopeptide according to claim 2, wherein said oligopeptide is in salt form.

10. The oligopeptide according to claim 3, wherein said oligopeptide is in salt form.

11. The oligopeptide according to claim 2, wherein the terminal carboxyl group of said oligopeptide is the acetate salt of an amide.

12. The oligopeptide according to claim 3, wherein the terminal carboxyl group of said oligopeptide is the acetate salt of an amide.

13. The oligopeptide according to claim 4, wherein the terminal carboxyl group of said oligopeptide is the acetate salt of an amide.

14. A pharmaceutical composition comprising an oligopeptide as in any of claims 1, 2-7, 8, 9, 10 or 11-13, further comprising a pharmaceutically acceptable medium.

15. The pharmaceutical composition according to claim 14, wherein said pharmaceutically acceptable medium comprises an excipient.

16. The pharmaceutical composition according to claim 15, wherein said excipient comprises mannitol.

* * * * *

```
                    SEQUENCE LISTING

<160> NUMBER OF SEQ ID NOS: 42

<210> SEQ ID NO 1
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Xaa at positions 2-4 can be any amino acid
<220> FEATURE:
<221> NAME/KEY: MISC_FEATURE
<222> LOCATION: (6)..(9)
<223> OTHER INFORMATION: The Xaa at positions 6-9 can be any amino acid

<400> SEQUENCE: 1

Arg Xaa Xaa Xaa Arg Xaa Xaa Xaa Xaa Tyr
1               5                   10

<210> SEQ ID NO 2
<211> LENGTH: 9
<212> TYPE: PRT
<213> ORGANISM: Artificial
<220> FEATURE:
<223> OTHER INFORMATION: Synthetic

<400> SEQUENCE: 2

Gly Leu Arg Ile Leu Leu Leu Lys Val
1               5

<210> SEQ ID NO 3
<211> LENGTH: 8
<212> TYPE: PRT
<213> ORGANISM: Artificial
<220> FEATURE:
<223> OTHER INFORMATION: Synthetic

<400> SEQUENCE: 3

Met Gly Leu Arg Ile Leu Leu Leu
1               5

<210> SEQ ID NO 4
<211> LENGTH: 8
<212> TYPE: PRT
<213> ORGANISM: Artificial
<220> FEATURE:
<223> OTHER INFORMATION: Synthetic

<400> SEQUENCE: 4

Leu Gly Ile Leu Leu Leu Gly Val
1               5

<210> SEQ ID NO 5
<211> LENGTH: 8
```

```
<212> TYPE: PRT
<213> ORGANISM: Artificial
<220> FEATURE:
<223> OTHER INFORMATION: Synthetic

<400> SEQUENCE: 5

Leu Asp Ile Leu Leu Leu Gly Val
1               5

<210> SEQ ID NO 6
<211> LENGTH: 9
<212> TYPE: PRT
<213> ORGANISM: Artificial
<220> FEATURE:
<223> OTHER INFORMATION: Synthetic

<400> SEQUENCE: 6

Leu Arg Ile Leu Leu Leu Ile Leu Val
1               5

<210> SEQ ID NO 7
<211> LENGTH: 7
<212> TYPE: PRT
<213> ORGANISM: Artificial
<220> FEATURE:
<223> OTHER INFORMATION: Synthetic

<400> SEQUENCE: 7

Leu Arg Leu Leu Leu Lys Val
1               5

<210> SEQ ID NO 8
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 can be any basic amino
      acid
<220> FEATURE:
<221> NAME/KEY: MISC_FEATURE
<222> LOCATION: (2)..(4)
<223> OTHER INFORMATION: The Xaa at positions 2-4 can be any amino acid
      other than an aliphatic polar amino acid
<220> FEATURE:
<221> NAME/KEY: MISC_FEATURE
<222> LOCATION: (5)..(5)
<223> OTHER INFORMATION: The Xaa at position 5 can be any basic amino
      acid
<220> FEATURE:
<221> NAME/KEY: MISC_FEATURE
<222> LOCATION: (6)..(8)
<223> OTHER INFORMATION: The Xaa at positions 6-8 can be any amino acid
      other than an aliphatic polar amino acid
<220> FEATURE:
<221> NAME/KEY: MISC_FEATURE
<222> LOCATION: (9)..(9)
<223> OTHER INFORMATION: The Xaa at position 9 is glycine, or any basic
      amino acid, or an aliphatic hydrophobic amino acid of from 5 to 6
      carbon atoms

<400> SEQUENCE: 8

Xaa Xaa Xaa Xaa Xaa Xaa Xaa Xaa Xaa Tyr
1               5                   10

<210> SEQ ID NO 9
<211> LENGTH: 10
<212> TYPE: PRT
```

```
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The Xaa at position 1 is a basic amino acid,
      preferably lysine or arginine, particularly arginine at at least
      one position and preferably both positions
<220> FEATURE:
<221> NAME/KEY: MISC_FEATURE
<222> LOCATION: (2)..(4)
<223> OTHER INFORMATION: The Xaa at positions 2-4 is any amino acid
      other than an aliphatic charged amino acid, preferably any amino
      acid other than a polar amino acid
<220> FEATURE:
<221> NAME/KEY: MISC_FEATURE
<222> LOCATION: (5)..(5)
<223> OTHER INFORMATION: The Xaa at position 5 is a basic amino acid,
      preferably lysine or arginine, particularly arginine at at least
      one position and preferably both positions
<220> FEATURE:
<221> NAME/KEY: MISC_FEATURE
<222> LOCATION: (6)..(8)
<223> OTHER INFORMATION: The Xaa at positions 6-8 is any amino acid
      other than an aliphatic charged amino acid, preferably any amino
      acid other than a polar amino acid
<220> FEATURE:
<221> NAME/KEY: MISC_FEATURE
<222> LOCATION: (9)..(9)
<223> OTHER INFORMATION: The Xaa at position 9 is glysine, or any basic
      amino acid, or an aliphatic hydrophobic amino acid of from 5 to 6
      carbon atoms, particularly glysine or any basic amino acid
<220> FEATURE:
<221> NAME/KEY: MISC_FEATURE
<222> LOCATION: (9)..(9)
<223> OTHER INFORMATION: The Xaa at position 9 is glysine, or any basic
      amino acid, or an aliphatic hydrophobic amino acid of from 5 to 6
      carbon atoms

<400> SEQUENCE: 9

Xaa Xaa Xaa Xaa Xaa Xaa Xaa Xaa Xaa Tyr
1               5                   10

<210> SEQ ID NO 10
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: The Xaa at positions 1 and 5 is any basic amino
      acid, preferably lysine or arginine, particularly arginine at at
      least one position, preferably at both positions
<220> FEATURE:
<221> NAME/KEY: MISC_FEATURE
<222> LOCATION: (2)..(8)
<223> OTHER INFORMATION: The Xaa at positions 2-4 and 6-8 are aliphatic
      amino acids of preferably of from 5 to 6 carbon atoms, more
      preferably at least 4 are aliphatic amino acids of from 5 to 6
      carbon atoms, more particularly 6 carbon atoms
<220> FEATURE:
<221> NAME/KEY: MISC_FEATURE
<222> LOCATION: (9)..(9)
<223> OTHER INFORMATION: The Xaa at position 9 is glysine, or any basic
      amino acid, or an aliphatic hydrophobic amino acid of from 5 to 6
      carbon atoms

<400> SEQUENCE: 10

Xaa Xaa Xaa Xaa Xaa Xaa Xaa Xaa Xaa Tyr
1               5                   10

<210> SEQ ID NO 11
```

```
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: The Xaa at position 2 is an uncharged aliphatic
      amino acid or aromatic amino acid, particularly a non-polar
      aliphatic amino acid or aromatic amino acid
<220> FEATURE:
<221> NAME/KEY: MISC_FEATURE
<222> LOCATION: (3)..(4)
<223> OTHER INFORMATION: The Xaa at positions 3-4 is any amino acid
      other than an aliphatic charged amino acid, preferably any amino
      acid other than a polar amino acid
<220> FEATURE:
<221> NAME/KEY: MISC_FEATURE
<222> LOCATION: (6)..(8)
<223> OTHER INFORMATION: The Xaa at positions 6-8 is any amino acid
      other than an aliphatic charged amino acid, preferably any amino
      acid other than a polar amino acid
<220> FEATURE:
<221> NAME/KEY: MISC_FEATURE
<222> LOCATION: (9)..(9)
<223> OTHER INFORMATION: The Xaa at position 9 is glycine, or any basic
      amino acid, or an aliphatic hydrophobic amino acid of from 5 to 6
      carbon atoms

<400> SEQUENCE: 11

Arg Xaa Xaa Xaa Arg Xaa Xaa Xaa Xaa Tyr
1               5                   10

<210> SEQ ID NO 12
<211> LENGTH: 10
<212> TYPE: PRT
<213> ORGANISM: Artificial
<220> FEATURE:
<223> OTHER INFORMATION: Synthetic

<400> SEQUENCE: 12

Arg Glu Asn Leu Arg Ile Ala Leu Arg Tyr
1               5                   10

<210> SEQ ID NO 13
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: The Xaa at positions 2-4 is norleucine
<220> FEATURE:
<221> NAME/KEY: MISC_FEATURE
<222> LOCATION: (6)..(8)
<223> OTHER INFORMATION: The Xaa at positions 6-8 is norleucine

<400> SEQUENCE: 13

Arg Xaa Xaa Xaa Arg Xaa Xaa Xaa Gly Tyr
1               5                   10

<210> SEQ ID NO 14
<211> LENGTH: 10
<212> TYPE: PRT
<213> ORGANISM: Artificial
<220> FEATURE:
<223> OTHER INFORMATION: Synthetic

<400> SEQUENCE: 14
```

```
Arg Val Asn Leu Arg Ile Ala Leu Arg Tyr
1               5                   10
```

<210> SEQ ID NO 15
<211> LENGTH: 10
<212> TYPE: PRT
<213> ORGANISM: Artificial
<220> FEATURE:
<223> OTHER INFORMATION: Synthetic

<400> SEQUENCE: 15

```
Arg Leu Leu Leu Arg Leu Leu Leu Gly Tyr
1               5                   10
```

<210> SEQ ID NO 16
<211> LENGTH: 10
<212> TYPE: PRT
<213> ORGANISM: Artificial
<220> FEATURE:
<223> OTHER INFORMATION: Synthetic

<400> SEQUENCE: 16

```
Arg Val Leu Leu Arg Leu Leu Leu Gly Tyr
1               5                   10
```

<210> SEQ ID NO 17
<211> LENGTH: 10
<212> TYPE: PRT
<213> ORGANISM: Artificial
<220> FEATURE:
<223> OTHER INFORMATION: Synthetic

<400> SEQUENCE: 17

```
Arg Ile Leu Leu Arg Leu Leu Leu Gly Tyr
1               5                   10
```

<210> SEQ ID NO 18
<211> LENGTH: 10
<212> TYPE: PRT
<213> ORGANISM: Artificial
<220> FEATURE:
<223> OTHER INFORMATION: Synthetic

<400> SEQUENCE: 18

```
Arg Leu Val Leu Arg Leu Leu Leu Gly Tyr
1               5                   10
```

<210> SEQ ID NO 19
<211> LENGTH: 10
<212> TYPE: PRT
<213> ORGANISM: Artificial
<220> FEATURE:
<223> OTHER INFORMATION: Synthetic

<400> SEQUENCE: 19

```
Arg Leu Ile Leu Arg Leu Leu Leu Gly Tyr
1               5                   10
```

<210> SEQ ID NO 20
<211> LENGTH: 10
<212> TYPE: PRT
<213> ORGANISM: Artificial
<220> FEATURE:
<223> OTHER INFORMATION: Synthetic

<400> SEQUENCE: 20

Arg Leu Leu Val Arg Leu Leu Leu Gly Tyr

-continued

```
<210> SEQ ID NO 21
<211> LENGTH: 10
<212> TYPE: PRT
<213> ORGANISM: Artificial
<220> FEATURE:
<223> OTHER INFORMATION: Synthetic

<400> SEQUENCE: 21

Arg Leu Leu Ile Arg Leu Leu Leu Gly Tyr
1               5                   10

<210> SEQ ID NO 22
<211> LENGTH: 10
<212> TYPE: PRT
<213> ORGANISM: Artificial
<220> FEATURE:
<223> OTHER INFORMATION: Synthetic

<400> SEQUENCE: 22

Arg Leu Leu Leu Arg Val Leu Leu Gly Tyr
1               5                   10

<210> SEQ ID NO 23
<211> LENGTH: 10
<212> TYPE: PRT
<213> ORGANISM: Artificial
<220> FEATURE:
<223> OTHER INFORMATION: Synthetic

<400> SEQUENCE: 23

Arg Leu Leu Leu Arg Ile Leu Leu Gly Tyr
1               5                   10

<210> SEQ ID NO 24
<211> LENGTH: 10
<212> TYPE: PRT
<213> ORGANISM: Artificial
<220> FEATURE:
<223> OTHER INFORMATION: Synthetic

<400> SEQUENCE: 24

Arg Leu Leu Leu Arg Leu Val Leu Gly Tyr
1               5                   10

<210> SEQ ID NO 25
<211> LENGTH: 10
<212> TYPE: PRT
<213> ORGANISM: Artificial
<220> FEATURE:
<223> OTHER INFORMATION: Synthetic

<400> SEQUENCE: 25

Arg Leu Leu Leu Arg Leu Ile Leu Gly Tyr
1               5                   10

<210> SEQ ID NO 26
<211> LENGTH: 10
<212> TYPE: PRT
<213> ORGANISM: Artificial
<220> FEATURE:
<223> OTHER INFORMATION: Synthetic

<400> SEQUENCE: 26

Arg Leu Leu Leu Arg Leu Leu Val Gly Tyr
1               5                   10
```

```
<210> SEQ ID NO 27
<211> LENGTH: 10
<212> TYPE: PRT
<213> ORGANISM: Artificial
<220> FEATURE:
<223> OTHER INFORMATION: Synthetic

<400> SEQUENCE: 27

Arg Leu Leu Leu Arg Leu Leu Ile Gly Tyr
1               5                   10

<210> SEQ ID NO 28
<211> LENGTH: 10
<212> TYPE: PRT
<213> ORGANISM: Artificial
<220> FEATURE:
<223> OTHER INFORMATION: Synthetic

<400> SEQUENCE: 28

Arg Trp Leu Leu Arg Leu Leu Leu Gly Tyr
1               5                   10

<210> SEQ ID NO 29
<211> LENGTH: 10
<212> TYPE: PRT
<213> ORGANISM: Artificial
<220> FEATURE:
<223> OTHER INFORMATION: Synthetic

<400> SEQUENCE: 29

Arg Leu Trp Leu Arg Leu Leu Leu Gly Tyr
1               5                   10

<210> SEQ ID NO 30
<211> LENGTH: 10
<212> TYPE: PRT
<213> ORGANISM: Artificial
<220> FEATURE:
<223> OTHER INFORMATION: Synthetic

<400> SEQUENCE: 30

Arg Leu Leu Trp Arg Leu Leu Leu Gly Tyr
1               5                   10

<210> SEQ ID NO 31
<211> LENGTH: 10
<212> TYPE: PRT
<213> ORGANISM: Artificial
<220> FEATURE:
<223> OTHER INFORMATION: Synthetic

<400> SEQUENCE: 31

Arg Leu Leu Leu Arg Trp Leu Leu Gly Tyr
1               5                   10

<210> SEQ ID NO 32
<211> LENGTH: 10
<212> TYPE: PRT
<213> ORGANISM: Artificial
<220> FEATURE:
<223> OTHER INFORMATION: Synthetic

<400> SEQUENCE: 32

Arg Leu Leu Leu Arg Leu Trp Leu Gly Tyr
1               5                   10
```

<210> SEQ ID NO 33
<211> LENGTH: 10
<212> TYPE: PRT
<213> ORGANISM: Artificial
<220> FEATURE:
<223> OTHER INFORMATION: Synthetic

<400> SEQUENCE: 33

Arg Leu Leu Leu Arg Leu Leu Trp Gly Tyr
1               5                   10

<210> SEQ ID NO 34
<211> LENGTH: 10
<212> TYPE: PRT
<213> ORGANISM: Artificial
<220> FEATURE:
<223> OTHER INFORMATION: Synthetic

<400> SEQUENCE: 34

Arg Tyr Leu Leu Arg Leu Leu Leu Gly Tyr
1               5                   10

<210> SEQ ID NO 35
<211> LENGTH: 10
<212> TYPE: PRT
<213> ORGANISM: Artificial
<220> FEATURE:
<223> OTHER INFORMATION: Synthetic

<400> SEQUENCE: 35

Arg Leu Tyr Leu Arg Leu Leu Leu Gly Tyr
1               5                   10

<210> SEQ ID NO 36
<211> LENGTH: 10
<212> TYPE: PRT
<213> ORGANISM: Artificial
<220> FEATURE:
<223> OTHER INFORMATION: Synthetic

<400> SEQUENCE: 36

Arg Leu Leu Tyr Arg Leu Leu Leu Gly Tyr
1               5                   10

<210> SEQ ID NO 37
<211> LENGTH: 10
<212> TYPE: PRT
<213> ORGANISM: Artificial
<220> FEATURE:
<223> OTHER INFORMATION: Synthetic

<400> SEQUENCE: 37

Arg Leu Leu Leu Arg Tyr Leu Leu Gly Tyr
1               5                   10

<210> SEQ ID NO 38
<211> LENGTH: 10
<212> TYPE: PRT
<213> ORGANISM: Artificial
<220> FEATURE:
<223> OTHER INFORMATION: Synthetic

```
<400> SEQUENCE: 38

Arg Leu Leu Leu Arg Leu Tyr Leu Gly Tyr
1               5                   10

<210> SEQ ID NO 39
<211> LENGTH: 10
<212> TYPE: PRT
<213> ORGANISM: Artificial
<220> FEATURE:
<223> OTHER INFORMATION: Synthetic

<400> SEQUENCE: 39

Arg Leu Leu Leu Arg Leu Leu Tyr Gly Tyr
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic

<400> SEQUENCE: 40

Arg Glu Asp Leu Arg Thr Leu Leu Arg Tyr
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic

<400> SEQUENCE: 41

Arg Glu Asn Leu Arg Ile Ala Leu Arg Tyr
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic

<400> SEQUENCE: 42

Arg Val Asn Leu Pro Ile Ala Leu Arg Tyr
1               5                   10
```